US006284746B1

(12) United States Patent
Szente et al.

(10) Patent No.: US 6,284,746 B1
(45) Date of Patent: Sep. 4, 2001

(54) INCLUSION COMPLEXES OF TAXOL OR TAXOTERE OR TAXUS EXTRACT FORMED WITH CYCLODEXTRINS, ITS PREPARATION AND USE

(75) Inventors: Lajos Szente; József Szejtli; Andrasne Vikmon, all of Budapest (HU)

(73) Assignee: Chinoin, Ltd., Budapest (HU)

( * ) Notice: Subject to any disclaimer, the term of this patent is extended or adjusted under 35 U.S.C. 154(b) by 0 days.

(21) Appl. No.: 08/545,721

(22) PCT Filed: May 9, 1994

(86) PCT No.: PCT/HU94/00012

§ 371 Date: Dec. 8, 1995

§ 102(e) Date: Dec. 8, 1995

(87) PCT Pub. No.: WO94/26728

PCT Pub. Date: Nov. 24, 1994

(30) Foreign Application Priority Data

May 12, 1993 (HU) .................................................. 93 01373

(51) Int. Cl.$^7$ .......................... A61K 31/715; C08B 37/16
(52) U.S. Cl. ............................................... 514/58; 536/103
(58) Field of Search .............................. 536/103; 514/58

(56) References Cited

U.S. PATENT DOCUMENTS

| 5,059,699 | * | 10/1991 | Kingston et al. | 549/511 |
| 5,278,324 | * | 1/1994 | Kingston et al. | 549/510 |
| 5,298,496 | | 3/1994 | Vikmon et al. | 514/58 |
| 5,439,686 | * | 8/1995 | Desai et al. | 424/451 |

FOREIGN PATENT DOCUMENTS

| 0 639 380 A1 | 2/1995 | (EP) . |
| 0371431B1 | 6/1995 | (EP) . |
| T052366T | 7/1990 | (HU) . |

OTHER PUBLICATIONS

Internal Medicine, 4th Edition, Editor–in–Chief Jay Stein, Chapters 71–72, pp. 699–715.*
Sigma Chemical Company, (1994), p. 962.

* cited by examiner

*Primary Examiner*—Gary Geist
*Assistant Examiner*—Everett White
(74) *Attorney, Agent, or Firm*—Birch, Stewart, Kolasch & Birch, LLP

(57) ABSTRACT

The present invention relates to an active inclusion complex of Taxol, Taxotere or a Taxus extract formed with a cyclodextrin-derivative, a pharmaceutical composition containing the same, a process of preparation and a method of treatment.

18 Claims, No Drawings

INCLUSION COMPLEXES OF TAXOL OR TAXOTERE OR TAXUS EXTRACT FORMED WITH CYCLODEXTRINS, ITS PREPARATION AND USE

The invention relates to the inclusion complexes of Taxol [2aR-[2aα, 4β;4αβ,6β,9α(αR*,βS*),11α–12α,12aα, 12bα]]-β-(Benzoylamino)-α-hydroxybenzene-propanoic acid 6,12-b-bis (acetyloxy)-12-(benzoyloxy)-2a,3,4,4a, 5,6, 9,10,11,12,12a,12b-dodecahydro-4,11-dihyroxy-4a,8,13, 13-tetramethyl-5-oxo-7,11-methano-1H-cyclodeca[3,4]-benz-[1,2-b]oxet-9-yl ester or Taxotere (butoxycarbonyl-10-deacetyl-N-debenzoyl taxol) and Taxus extracts (comprising besides taxol other diterpene taxan-derivatives such as cephalomannine, 10-deacetyl-taxol, deacetyl baccatine-III, baccatine-III, cinnamoyl-taxicines, taxusine) formed with a cyclodextin derivative or cyclodextrin-derivative-mixture.

Even though taxol shows a rather promising biological effectivity and significant antitumor activity, it's therapeutical application is associated with a lot of difficulties:

- taxans are very slightly soluble in water, for exanple the water solubility of taxol is between 0.55–0.59 μg/ml at 25° C. (determined at Cyclolab)
- taxol is very sensitive to light and the pH, during. its decomposition biologically inactive products are forming.
- results given on taxol in pharmacology are challenged of validity because of the cytotoxic solvents used (Cremophor EL) /Denis, J. N: J.Am. Chem. Soc. 110. 5917. 1988 and Fjaellskog M. L. et al.: Lancet, 342–873. 1993 and Webster, L. et al.: J. Natl. Cancer Inst. 85. 1685. 1993.

Numerous processes are known to improve the disadvantageous features mentioned above:

- Using solubilizing agents (mixture of Cremophor EL—anhydrous ethanol in the rate of 1:1, Natl. Cancer Institute, PACLITAXEL Documentation);
- Forming chemically modified micromicelles using phosphatydil-ethanolamines (Patent of Lipid Specialities, Inc. EP 118 316)
- Using mixtures of ethanol-polysorbates as solubility increasing agents (Patent of Rhone-Poulenc Rorer EP 522 936, and Rhone Poulenc Rorer EP 522 937)
- Using Liposomal taxol formulations (e.g. Aquilar, R. and Rafaelloff, R. WO 93/18751 and Alkan, M. H. et al.: J. Liposome Research 3. 42. 1993.)

There were some trials to increase the water solubility of taxol by forming synthetic derivatives as well.(e.g. written by Zhao, H. et. al. J.Nat. Prod. 54.6. 1607. 1991., Kingston, D. I. Xang, Y. Y. EP Pat. Appl. EP 537905 and Deutsch, H. M. et al. U.S. Pat. No. 5.157.049)

The biological effectivity of the chemically modified, increased soluble taxol derivatives changes for the worse, mostly the multidrug-resistance shows an upward tendency and the cytotoxicity—just the biological effect—is diminished.

To solve difficulties during the parenteral application of taxol, Taxol-prodrugs with increased water solubility have also been synthetized. (Matthew A. et. al.: J.Med.Chem. 35. 1. 145 1992.).

By microencapsulating of tixol Bartoli et. al. wanted to improve the generally poor stability of it (Bartoli H; et. al.: J.Microencapsulation 7.2. 191. 1990).

There are a lot of difficulties in preparing especially the parenteral pharmaceutical products containing taxol, because the diterpenoid-type, rather lipophilic taxan-derivatives can not be formulated as suitable stable and concentrated solutions even in the presence of large amount of detergents and mixtures of water and organic solvents. /Tarr, B. Pharm. Res. 4.2. 162. 1987.

Nowadays the officially registered (for example at the National Institutes of Health and the National Cancer Institute) parenteral taxol-forms are formulated as 6 mg/ml concentrated emulsions in polyoxyethylated castor oil (Cremphor EL) and ethanol at the ratio of 1:1, and on application these emulsions have to be diluted tenfold. Application of these parenteral products is associated with numerous unpleasant side-effects among others the most important is the serious allergic by-effect caused in consequence of the parenterally hardly tolerable Cremophor EL. Moreover the taxol-formulations produced in Cremophor EL—ethanol solvent are not clear solutions but slightly opaline (Trissel, L. A.: Am.J. Hosp. Pharm. 50.300.1993) and at diluting or applying them together with some other pharmaceuticals there is a possibility of the formation of precipitation.

In a conference in Japan it was reported that glycosyl- and maltosyl-β-cyclodextrins used together with ethanol and ethylacetate increased the solubility of taxol up to 20–110 μg/ml (Mikuni, K. et. al.: 1993.)

According to our present invention, improved aqueous solubility of Taxol and taxan-derivatives can be reached by using suitable cyclodextrins and/or cyclodextrin derivatives and/or mixtures thereof without forming any chemical bonds between taxol and cyclodextrins.

The inclusion complexes of the present invention can be prepared by a.) reacting Taxol or Taxotere or a Taxus extract in an aqueous medium with a cyclodextrin derivative and isolating the complex from the mixture by means known per se.

b.) reacting Taxol or Taxotere or a Taxus extract with a cyclodextrin derivative in a solid form.

c.) high energy milling of Taxol or Taxotere or a Taxus extract with a cyclodextrin derivative.

The complex can be isolated from the mixture by filtration, centrifugation, lyophilization, spay-drying, or vacuum drying.

The high energy milling of Taxol or Taxotere or Taxus extract with a cyclodextrin derivative can be performed as described or referred to in the published Hungarian Patent Application No. T/52366.

As cyclodextrin derivatives preferably heptakis-2,6-0-dimethyl-β-cyclodextrin randomly methylated-β-cyclodextrin succinyl-methyl-β-cyclodextrin 2-hydroxy propyl-β-cyclodextin soluble anionic-β-cyclodextrin (CDPSI)

β-cyclodextrin

γ-cyclodextrin can be used.

Some of the inclusion complexes of the present invention have improved aqueous solubility and stability such as the inclusion complex of Taxol or Taxotere or a Taxus extract formed with heptakis-2,6-0-dimethyl-β-cyclodextrin randomly methylated-β-cyclodextrin succinyl-methyl-β-cyclodextrin so they can be used as active ingredients in pharmaceutical compositions.

The pharmaceutical compositions of the invention containing as active ingredient an effective amount of the inclusion complex of Taxol or Taxotere or a Taxus extract formed with a cyclodextrin derivative, preferably heptakis-2,6-0-dimethyl-β-cyclodextin, randomly methylated-β-cyclodextrin, succinyl-methyl-β-cyclodextrin and customary pharmaceutical filling, diluting and further auxiliary materials can be prepared in a manner known per se.

Other inclusion complexes of the present invention do not or do not significantly improve the aqueous solubility, such as the inclusion complex of Taxol or Taxotere or a Taxus extract formed with 2-hydroxy propyl-β-cyclodextrin soluble aninonic-β-cyclodextrin polymer (CDPSI), average molecular weight 6000–8000 daltons.

β-cyclodextrin

γ-cyclodextrin but they can be used e.g. to extract taxol from the ferment of taxol producing cells.

The invention is illustrated by the following examples without restricting the invention to them.

EXAMPLE 1

11.6 mg of Taxol (Sigma Chemicals Co. USA) is treated in 10 ml of 40% aqueous heptakis-2,6-di-O-methylated β-cyclodextrin at room temperature for 30 minutes, until a solution of slight haze is obtained. This solution is then filtered on sterile 0.22 μm cellulose acetate membrane filter, resulting in clear aqueous taxol solution in which the dissolved taxol concentration is 992–1000μg/ml. (the aqueous solubility of the taxol at 25° C. is otherwise 0.55–0.59 μg/ml)

The clear, sterile filtered aqueous taxol solutions can be stored under normal conditions without deterioration for eight weeks.

The above aqueous taxol solution can be freeze dried resulting in 3.94 g white, slight nearly amorphous solid product, that can be re-dissolved upon contacting with water. The reconstituted solution contains 1000 μg/ml dissolved taxol, and the pH of this solution is between 5.7–6.2. The existence of inclusion complex in solid state was proved by X-ray powder diffractometry and by Differential Scanning Calorimetry.

EXAMPLE 2

Randomly methylated β-cyclodextrin (average degree of substitution=1.8) was dissolved in physiological buffered saline (pH 7.6) at different concentrations and these solutions were incubated with the taxol substrate for 12 hours at room temperature. Each sample contained taxol in 5 mg/ml initial concentration. The suspensions after equilibration were membrane filtered and assayed for dissolved taxol by HPLC. The solubility data obtained are listed in Table 1.

TABLE 1

Aqueous solubility of taxol in randomly methylated βCD solutions of different concentrations.

| RAMEB (%) | dissolved taxol in μg/ml |
|---|---|
| none | 0.6 |
| 1 | 4.4 |
| 5 | 42.5 |
| 10 | 231.7 |
| 40 | 859.9 |

This solubility enhancement refers to the complex formation in solution between taxol and methyl-βCD, since glucose did not cause any solubility increase.

EXAMPLE 3

Taxol was solubilized in the presence of sulfopropyloxy-β-cyclodextrin in the same way as described in example 2.

The sulfopropyloxy-β-cyclodextrin was not found suitable for the solubilization of taxol under investigation conditions (25° C., in water, at neutral pH), in contrast, this derivative was found to interact with taxol in solution unfavorably, and due to this interaction taxol was found to decompose to unknown products.

EXAMPLE 4

Water soluble anionic-β-cyclodextrin polymer (epichlorohydrin-cross linked carboxymethylated-β-cyclodextrin, abbreviated as CDPSI) was found to be a less potent solubilizing agent than the methylated β-cyclodextrins. The solubility enhancements are listed in Table 2.

TABLE 2

Aqueous solubility's of taxol in presence of ionic water soluble β-cyclodextrin polymer

| CDPSI (%) | dissolved taxol in μg/ml |
|---|---|
| 0 | 0.6 |
| 1 | 1.8 |
| 5 | 3.5 |
| 10 | 10.6 |
| 40 | 56.8 |

EXAMPLE 5

Taxol was solubilized and formulated with 2-hydroxypropylated β-cyclodextrin. (HPBCD). The solubility enhancements achieved by HPBCD solutions are given in Table 3.

TABLE 3

Solubilizing of taxol with HPBCD

| HPBCD (%) | dissolved taxol μg/ml |
|---|---|
| none | 0.6 |
| 0.5 | 1.0 |
| 1 | 1.7 |
| 5 | 6.8 |
| 10 | 34.9 |
| 40 | 100.4 |

EXAMPLE 6

Mono-succinyl-methyl-β-cyclodextrin, an acidic function bearing methylated β-cyclodextrin was found to be a potent solubilizing agent for the improvement of aqueous solubility of taxol. in 1 ml of 10% aqueous solution of succinyl-methyl-β-Cyclodextrin taxol was stirred for 12 hour at room temperature. The suspension was filtered and the dissolved taxol determined by HPLC. The dissolved taxol concentration in 10% aqueous solution of succinyl-methyl-βCD was 244 μg/ml, while the 40% succinyl methyl-βCD solution enabled a dissolved taxol concentration of 993 μg/ml. Thus the solubilizing power of monosuccinyl-methyl-β-cyclodextrin was almost as high as that of the heptakis 2,6-di-O-methylated-β-cyclodextrin.

EXAMPLE 7

8.5 mg of taxol and 26.6 mg (about a 1:2 molar ratio) heptakis-2,6-di-O-methylated-βCD were intensively co-ground with 0.25 ml of ethanol:water 1:2 mixture until a homogeneous cream is obtained. The wet cream is dried on air to constant weight, and powdered. The resulting white solid contained 21.8% taxol. The in vitro dissolution properties of the entrapped taxol from product according to Example 7 was found to surpass significantly that of the non-complexed taxol, by 120–124 fold. Furthermore the chemical and heat stability of the taxol in this formulation was also improved.

EXAMPLE 8

8.5 mg of taxol and 52.9 mg of γ-cyclodextrin were stirred intensively in 2.5 ml of 33% (v/v) aqueous ethanol for 6 hours. The solvent is removed by freeze-drying that results in a white microcrystalline product. In the taxol/γ-cyclodextrin formulation the taxol had an improved stability against heat as proved by thermal analyses. On the DSC pattern of complex according to Example 8. no sign of the endothermic heat flow is detected in the melting range of taxol, which points to the complexed state of the drug. The crystalline taxol γCD formulation was found to be suitable for direct tabletting. The fact of the formation of novel crystalline lattice was proven by X-ray diffractometry, as well.

The interaction of taxoi and γCD did not result in any solubility enhancement, in contrast the effect of γCD was just opposite, thus the aqueous γCD solutions are able to remove taxol from multicomponent mixture (e.g. from Taxus brevifolia ground stem bark) by formation of stable crystalline complex, from which the entrapped taxol can be re-extracted.

EXAMPLE 9

50 mg of β-cyclodextrin and 8.5 mg of taxol were reacted in 2.5 ml of water-ethanol 1:2 mixture at room temperature for 12 hours. The solvent was removed by spray-drying or freeze-drying yielding a white microcrystalline solid, that revealed to novel crystalline state thus an inclusion complex by X-ray powder diffraction. The solid taxol/β-cyclodextrin formulation was found to be suitable for direct tabletting. The in vitro dissolution rate of taxol from βCD formulation was found to be better, than that of the free taxol both in water and in pH 7.6 buffer.

EXAMPLE 10

The solubilization of a synthetic taxol analog, Taxotere (butoxycarbonyl-10-deacetyl-N-debenzoyl taxol) was carried out by stirring intensively the 2.5 mg of Taxotere in 1 ml of 40% aqueous randomly methylated-β-cyclodextrin (DS=1.8) at 25° C. for 12 hours. The solubility enhancement achieved by this way was 850 times that of the free taxol derivative in water. The freeze dried product according to Example 10 is a white amorphous powder, that showed a good wettability and improved aqueous solubility under normal conditions. The solubility enhancement achieved by methylated β-cyclodextrin proved the existence of inclusion complex in solution. (The same concentration of glucose did not improve the solubility of Taxotere.)

EXAMPLE 11

A dilutable concentrated solution containing taxol and solubilizer according to the present invention:
- 10 mg taxol (Signa Chemicals No. T-7402, Lot. No.23H0464)
- 10 ml 40% aqueous solution of crystalline heptakis 2,6-di-O-methyl/β-cyciodextrin are stirred for 12 hours under nitrogen, protected from light. The resulting clear solution is then sterile filtered across a 0.22 μm membrane into a sterile injection ampoule and sealed. The sterile solution is useful for further dilution with physiologically acceptable diluents to desired concentration and the solution is stable for two months. (the loss of active ingredient in solution after a 60-day storage at 25° C. was found to be less, than 3%)

EXAMPLE 12

Taxol containing hydrogel is prepared by dissolving 1 mg of taxol (Sigma Chemicals No. T-7402, Lot.No. 23H0464) in 1 ml of 40% randomly methylated-β-cyclodextrin and this solution is mixed with 25 mg of methyl cellulose exhaustively for 30 minutes to obtain a transparent colorless topical useful gel which has no irritation to human skin and preserves well the dissolved taxol.

What we claim is:

1. Inclusion complex of Taxol [2aR-[2aα,4β;4αβ,6β,9α (αR*,βS*), 11α–12α,12aα,12bα]]-β-(Benzoylamino)-α-hydroxybenzene-propanoic acid 6,12-b-bis (acetyloxy)-12-(benzoyloxy)-2a,3,4,4a,5,6,9,10,11,12,12a,12b-dodecahydro-4,11-dihyroxy-4a,8,13,13-tetramethyl-5-oxo-7,11-methano-1H-cyclodeca [3,4]-benz-[1,2-b]oxet-9-yl ester or Taxotere (butoxycarbonyl-10-deacetyl-N-debenzoyl taxol) or Taxus extracts formed with a cyclodextrin derivative.

2. Inclusion complex of Taxol with a cyclodextrin derivative.

3. Inclusion complex of a Taxus brevifolia solvent free extract comprising besides Taxol other diterpene taxan-derivatives with a cyclodextrin derivative.

4. The inclusion complex of claim 3, wherein said other diterpene taxan derivatives are selected from the group consisting of cephalomannine, 10-deacetyl-taxol; deacetyl baccatine-III; baccatine-III, cinnamoyl-taxicines; and taxusine.

5. Inclusion complex of Taxol or Taxotere or a Taxus brevifolia extract formed with heptakis-2,6-0-dimethyl-β-cyclodextrin.

6. Inclusion complex of Taxol or Taxotere or a Taxus brevifolia extract formed with randomly methylated-β-cyclodextrin.

7. Inclusion complex of Taxol or Taxotere or a Taxus brevifolia extract formed with succinyl-methyl-β-cyclodextrin.

8. Inclusion complex of Taxol or Taxotere or a Taxus brevifolia extract formed with 2-hydroxy propyl-β-cyclodextrin.

9. Inclusion complex of Taxol or Taxotere or a Taxus brevifolia extract formed with a soluble anionic-β-cyclodextrin-polymer.

10. The inclusion complex of claim 9, wherein said soluble anionic-β-cyclodextrin-polymer has an average molecular weight of 6000–8000.

11. Inclusion complex of Taxol or Taxotere or a Taxus brevifolia extract formed with β-cyclodextrin.

12. Inclusion complex of Taxol or Taxotere or a Taxus brevifolia extract formed with γ-cyclodextrin.

13. Process for the preparation of the inclusion complex of Taxol or Taxotere or a Taxus brevifolia extract formed with a cyclodextrin-derivative which comprises:
   a.) reacting Taxol or Taxotere or a Taxus brevifolia extract in an aqueous medium with a cyclodextrin derivative and isolating the complex from the mixture,
   b.) reacting Taxol or Taxotere or a Taxus brevifolia extract with a cyclodextrin derivative in a solid form, or
   c.) high energy milling of Taxol or Taxotere or a Taxus brevifolia extract with a cyclodextrin derivative.

14. Process according to claim 13, wherein the complex is isolated from the mixture by filtration, centrifugation, lyophilization, spay-drying, or vacuum drying.

15. Pharmaceutical composition comprising as active ingredient an effective amount of the inclusion complex of Taxol or Taxotere or a Taxus extract formed with a cyclodextrin derivative, and conventional pharmaceutical filling, diluting and further auxiliary materials.

16. The pharmaceutical composition of claim 15, wherein the cyclodextrin derivative is selected from the group consisting of heptakis-2,6-0-dimethyl-β-cyclodextrin, randomly methylated-β-cyclodextrin, and succinyl-methyl-β-cyclodextrin.

17. Method of treatment of cancer in humans orally, parenterally which comprises administering to the human an effective amount of an inclusion complex of Taxol or Taxotere or Taxus extract formed with a cyclodextrin derivative.

18. The method of claim 17, wherein the cyclodextrin derivative is selected from the group consisting of heptakis-2,6-0-dimethyl-β-cyclodextrin, randomly methylated-β-cyclodextrin, and succinyl-methyl-β-cyclodextrin.

* * * * *